US006699180B2

(12) United States Patent
Kobayashi

(10) Patent No.: US 6,699,180 B2
(45) Date of Patent: Mar. 2, 2004

(54) ENDOSCOPIC HOOD

(75) Inventor: Tsukasa Kobayashi, Hachioji (JP)

(73) Assignee: Olympus Corporation, Tokyo (JP)

( * ) Notice: Subject to any disclaimer, the term of this patent is extended or adjusted under 35 U.S.C. 154(b) by 11 days.

(21) Appl. No.: 10/115,602

(22) Filed: Apr. 3, 2002

(65) Prior Publication Data
US 2003/0191365 A1 Oct. 9, 2003

(51) Int. Cl.[7] ............................... A61B 1/00
(52) U.S. Cl. ........................ 600/127; 600/104
(58) Field of Search .................. 600/127, 128, 600/106, 107, 104, 129, 153

(56) References Cited

U.S. PATENT DOCUMENTS

| | | | | |
|---|---|---|---|---|
| 4,436,087 A | * | 3/1984 | Ouchi | 600/106 |
| 5,827,175 A | * | 10/1998 | Tanaka | 600/104 |
| 6,454,702 B1 | * | 9/2002 | Smith | 600/104 |
| 6,524,234 B2 | * | 2/2003 | Ouchi | 600/127 |

FOREIGN PATENT DOCUMENTS

| | | |
|---|---|---|
| DE | 28 53 466 C2 | 6/1979 |
| JP | 8-131397 | 5/1996 |
| JP | 9-66019 | 3/1997 |

* cited by examiner

*Primary Examiner*—John Mulcahy
(74) *Attorney, Agent, or Firm*—Scully, Scott, Murphy & Presser

(57) ABSTRACT

A rotation restricting section is provided at an inner surface of a cap attached to a distal end portion of an insertion section of an endoscope and is set in abutting contact with a treating tool projected from the distal end of the inserting section to restrict the treating tool from being rotated about an axial direction of the insertion section.

15 Claims, 6 Drawing Sheets

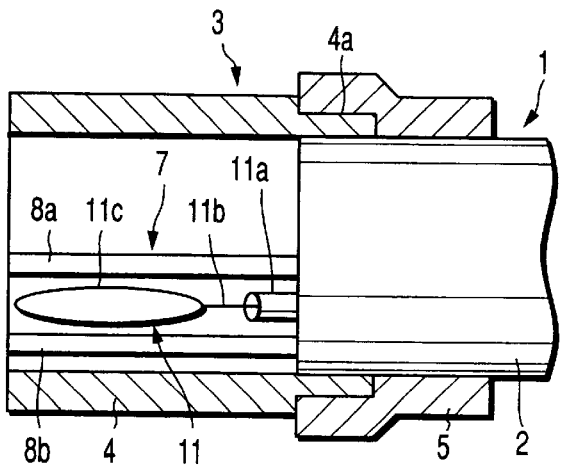
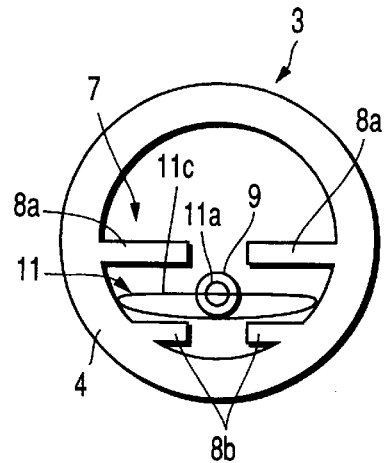
FIG. 3A　　　　　　　　　　FIG. 3B
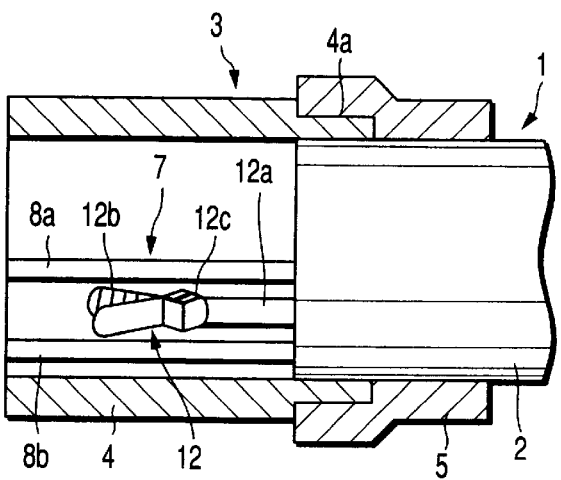
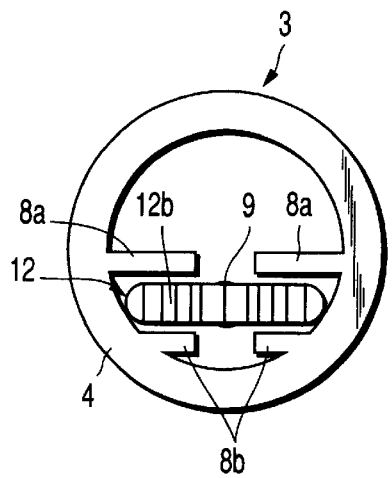
FIG. 4A　　　　　　　　　　FIG. 4B

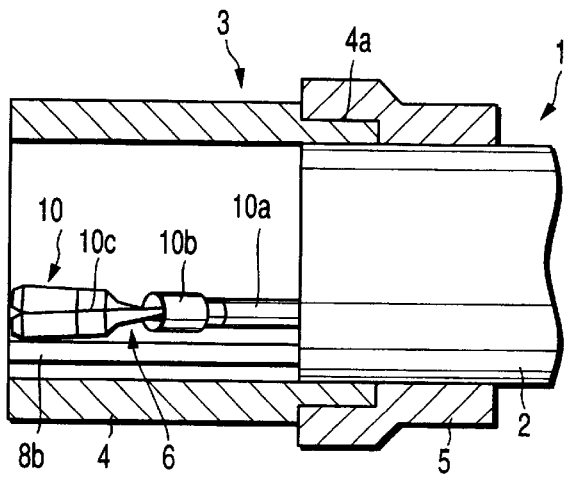
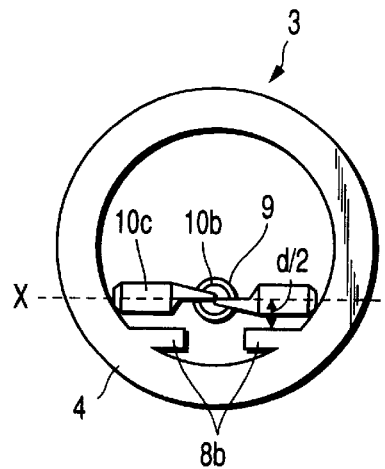
FIG. 5A  FIG. 5B
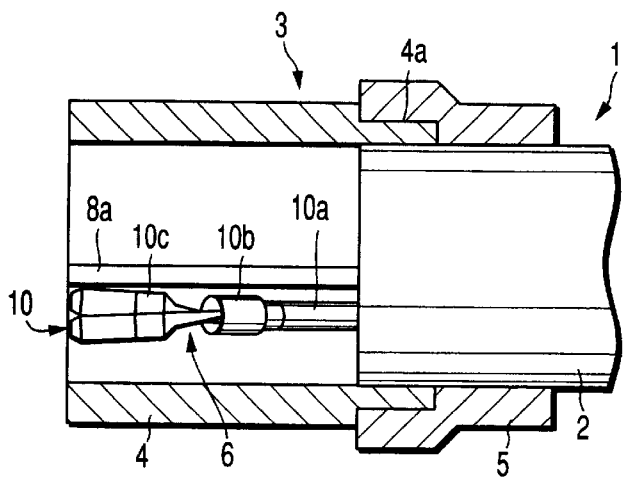
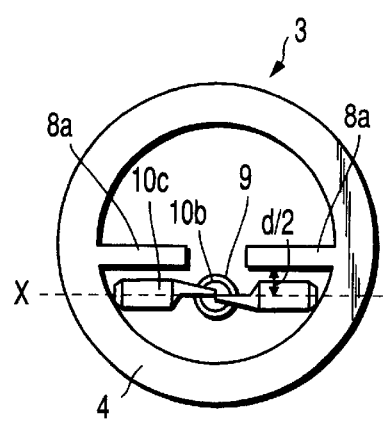
FIG. 6A  FIG. 6B

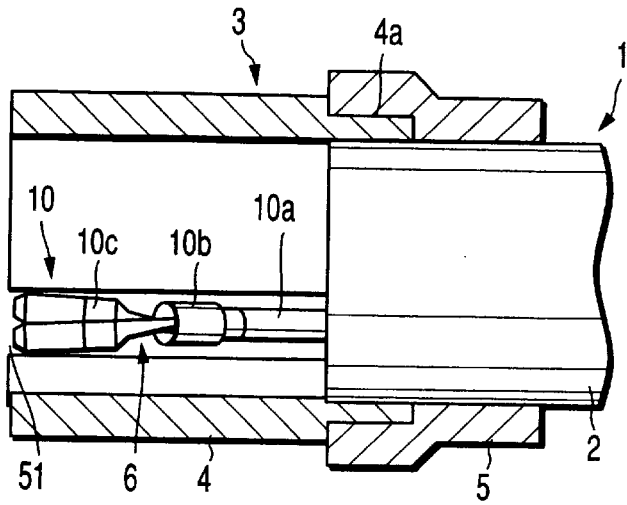
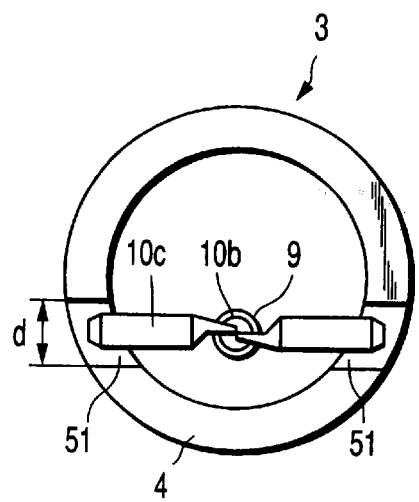
FIG. 11A  FIG. 11B
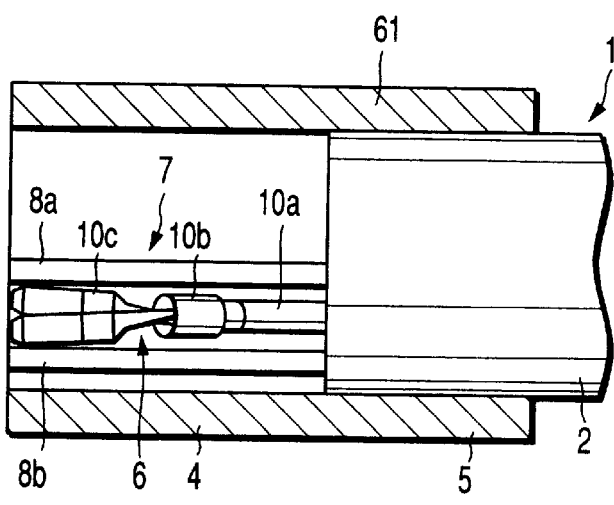
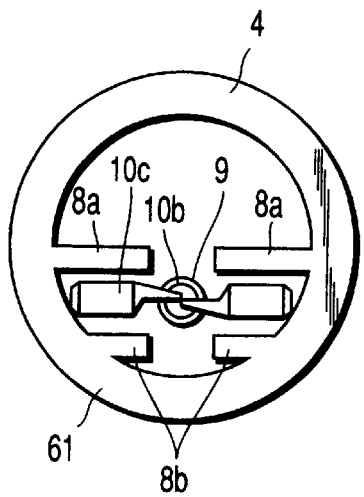
FIG. 12A  FIG. 12B

ENDOSCOPIC HOOD

BACKGROUND OF THE INVENTION

The present invention relates to an endoscopic hood which is attached to a distal end of an insertion section of an endoscope and, when the endoscope is inserted into a body cavity of a patient, protects the forward end portion of an insertion section of the endoscope.

Generally, upon an examination and surgery under an endoscope, a treating tool is used which is inserted into a body cavity of a patient via a tool insertion channel of the endoscope. As the treating tool for an endoscope there is a treating tool of such a type as to grasp a living tissue, such as a clipping device, a high frequency snare, grasping forceps as well as a biopsy forceps.

When the grasping or clipping procedure is performed with the use of this type of treating tool, the endoscope itself or the treating tool itself is moved or rotated, so that the distal end of the treating tool is so operated as to be directed toward a desired direction. And such procedure is performed to fix the tool to a given position with the distal end of the treating tool oriented toward a desired direction. For this reason, for the treating tool for grasping or clipping a living tissue it is important to set a direction in which the living tissue is grasped or clipped.

For example, Jpn. Pat. Appln. KOKAI Publication Nos. 8-131397 and 9-66019 disclose a structure in which, upon examination and surgery under an endoscope, an endoscopic hood of a substantially cylindrical configuration is detachably mounted to the distal end of the insertion section of the endoscope. In this case, the treating tool inserted into an inside of a body of a patient via a tool insertion channel of an endoscope is projected toward a front direction from the distal end of an endoscopic hood.

Further, the inner surface of the endoscopic hood of a conventional structure is formed to have a substantially smooth wall surface. For this reason, the treating tool slips upon being contacted with the inner wall surface of the endoscopic hood and is retained in a state to be freely rotatable about an axial direction of the insertion section of the endoscope. Even if, therefore, the distal end of the treating tool is correctly oriented toward a desired direction, the endoscope itself may be rotated, or the treating tool may be rotated about an axial direction of the insertion section of the endoscope, due to an action of an operation force upon the treating tool when the living tissue is grasped or clipped by the treating tool. In this situation, the distal end of the treating tool cannot be correctly retained toward an intended direction. For this reason, it takes a lot of time to fixedly orient the distal end of the treating tool toward the desired direction and it also takes a lot of a skill to perform such an operation.

BRIEF SUMMARY OF THE INVENTION

It is accordingly an object of the present invention to provide an endoscopic hood which can restrict the distal end of a treating tool from being rotated about its axial direction and orient the tool toward a desired direction and do this treating procedure quickly and accurately.

In order to achieve the above-mentioned object of the present invention, the invention of claim 1 provides an endoscopic hood having a substantially cylindrical cap attached to a distal end of an insertion section of an endoscope to protect the distal end of an insertion section of the endoscope, the cap having a rotation restricting section in its inner surface which, when a treating tool is projected from the distal end of the insertion section of the endoscope, abuts against the treating tool to restrict the treating tool from being rotated about an axial direction of the insertion section of the endoscope.

According to the invention of claim 1, the treating tool projected from the distal end of the insertion section of the endoscope is set in abutting engagement with the rotation restricting section of the inner surface of the cap attached to the distal end of the endoscope. By doing so, the treating tool is restricted from being rotated about the axial direction of the insertion section of the endoscope. Further, after inserting the endoscope into a body cavity of a patient, the distal end of the treating tool held within the cap is projected onto a living tissue or, with the living tissue drawn into the cap, the distal end of the treating tool is abutted against the living tissue and the tool grasps or clips the living tissue.

According to the present invention, therefore, the distal end of the treating tool is initially restricted from being rotated about the axial direction and can be correctly oriented toward a desired direction, so that it is possible to perform a correct treatment quickly.

The invention of claim 2 is such that, in the endoscopic hood of claim 1, the rotation restricting section is comprised of a projection projected toward an inner direction on the inner surface of the cap.

According to the invention of claim 2, the treating tool projected from the distal end of the insertion section of the endoscope is set in abutting engagement with the projection of the rotation restricting section of the inner surface of the cap attached to the distal end of the insertion section of the endoscope. By doing so, the treating tool is restricted from being rotated about the axial direction of the insertion section of the endoscope.

The invention of claim 3 is such that, in the endoscopic hood of claim 2, the projection is comprised of a planar surface with a portion of the inner wall surface of the cap raised toward a center direction.

According to the invention of claim 3, the treating tool projected from the distal end of the insertion section of the endoscope is set in abutting engagement with the projection of the rotation restricting section which is raised toward the center direction at a portion of the inner wall surface of the cap attached to the distal end of the insertion section of the endoscope. By doing so, the treating tool is restricted from being rotated about the axial direction of the insertion section of the endoscope.

The invention of claim 4 is such that, in the endoscopic hood of claim 1, the rotation restricting section is comprised of a wall groove section provided by cutting the wall of the cap from an inner wall surface side to an outer wall surface side.

The invention of claim 4 is such that the treating tool projected from the distal end of the insertion section of the endoscope is set into abutting engagement with the wall groove section of the rotation restricting section provided by cutting the wall of the cap from an inner wall surface side to an outer wall surface side, the cap being attached to the distal end portion of the insertion section of the endoscope. By doing so, the treating tool is restricted from being rotated about the axial direction of the insertion section of the endoscope.

The invention of claim 5 is such that, in the endoscopic hood of claim 1, the cap is made of a hard material and has a fixing cylindrical body for fixing the distal end portion of the insertion section of the endoscope to an outer peripheral surface of a proximal end side thereof.

According to the invention of claim 5, the fixing cylindrical body at the outer peripheral surface of the proximal end side of the cap made of the hard material is fixed to the distal end portion of the insertion section of the endoscope. By doing so, the hard cap is attached to the distal end portion of the insertion section of the endoscope.

The invention of claim 6 is directed to a method of using an endoscopic hood which has a substantially cylindrical cap fixed to an endoscope, the cap being attached to a distal end portion of the insertion section of the endoscope to protect the distal end portion of the insertion section of the endoscope. In the method, the cap has a rotation restricting section at an inner wall surface thereof which is set in abutting contact with a treating tool when the treating tool is projected from the distal end of the insertion section of the endoscope, and restricts the treating tool from being rotated about an axial direction of the insertion section of the endoscope. The cap is so attached to align a line, which is drawn from a center of the distal end of the endoscope to a center of a channel, with a line which is drawn in a manner to set a cross-sectional configuration of the cap in a mirror image relation.

The invention of claim 7 is such that, in the method for using an endoscopic hood of claim 6, when the cap is used, the distal end of the treating tool is opened in a mutually opposite directions to restrict a rotation of the distal end of the treating tool.

BRIEF DESCRIPTION OF THE SEVERAL VIEWS OF THE DRAWING

FIG. 3A is a longitudinal cross-sectional view showing a major section in a state in which a high frequency snare is inserted into the endoscopic hood of the first embodiment;

FIG. 3B is a front view showing an endoscopic hood in a state in which the high frequency snare inserted into the endoscopic hood has its rotation restricted;

FIG. 4A is a longitudinal cross-sectional view showing a major section in a state in which a grasping forceps is inserted into the endoscopic hood of the first embodiment;

FIG. 4B is a front view of the endoscopic hood in a state in which the grasping forceps inserted into the endoscopic hood of the first embodiment has its rotation restricted;

FIG. 5A is a longitudinal cross-sectional view showing a major section in a state in which a clipping device is inserted into an endoscopic hood as a first variant of the endoscopic hood of the first embodiment;

FIG. 5B is a front view of the endoscopic hood in a state in which the clipping device inserted into the endoscopic hood of the first variant has its rotation restricted;

FIG. 6A is a longitudinal cross-sectional view showing a major section in a state in which a clipping device is inserted into an endoscopic hood as a second variant of the endoscopic hood of the first embodiment;

FIG. 6B is a front view showing a state in which the clipping device inserted into the endoscopic hood of the second variant has its rotation restricted;

FIG. 11A is a longitudinal cross-sectional view showing a major section in a state in which a clipping device is inserted into an endoscopic hood according to a sixth embodiment of the present invention;

FIG. 11B is a front view of the endoscopic hood in a state in which the clipping device inserted into the endoscopic hood of the sixth embodiment has its rotation restricted;

FIG. 12A is a longitudinal cross-sectional view showing a major section in a state in which a clipping device is inserted into an endoscopic hood according to a seventh embodiment of the present invention; and FIG. 12B is a front view of the endoscopic hood in a state in which the clipping device inserted into the endoscopic hood of the seventh embodiment has its rotation restricted.

DETAILED DESCRIPTION OF THE INVENTION

Figure 1A:
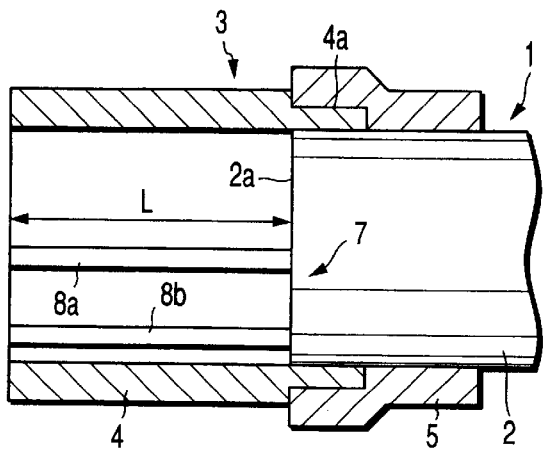
FIG. 1A is a longitudinal cross-sectional view showing a state in which an endoscopic hood of a first embodiment of the present invention is attached.

A first embodiment of the present invention will be described below with reference to FIGS. 1A through 4B. FIG. 1A shows a state in which an endoscopic hood 3 according to the present invention is mounted on a distal end portion of an insertion section 2 of an endoscope 1. The endoscopic hood 3 includes a substantially cylindrical cap 4 and a substantially cylindrical fixing body 5. The fixing cylindrical body 5 is comprised of a member for fixing the cap 4 to the distal end portion of the insertion section 2 of the endoscope 1.

Further, the cap 4 is formed of a rigid, transparent synthetic resin, such as an acryl resin, and preferably a transparent and hard plastic, such as polycarbonate. This structure does not prevent a visual field of the endoscope 1. It is to be noted that the cap 4 has a hardness to an extent not being easily deformed. For example, the hood 3 has a hardness to an extent which can firmly fix the rotation of a later-described treating tool, by its cap 4, at a time of pushing the hood 3 against a mucosa or sucking the mucosa and can retain it, at a sucking time, in such a state as to allow an adequate amount of mucosa to enter into the cap 4. A substantially ring-like engaging recess 4a of a smaller outer diameter is formed on an outer peripheral surface of a proximal end portion of the cap 4.

Further, the cylindrical fixing body 5 is made of a soft plastic material, such as vinyl chloride, polyurethane and fluorine resin, rubbers such as latex, silicone, isoprene and neoprene, or synthetic resin material. The distal end portion of the cylindrical fixing body 5 is press-fitted over the cap 4 in such a state as to be externally inserted over the engaging recess 4a of the cap 4. The joining portions of the outer section of the cylindrical fixing body 5 and the engaging recess 4a are connected together by an adhesive. It is to be noted that the fixing of the cap 4 and cylindrical fixing body 5 may be made by means of a screw, etc., or may be more firmly made with the use of an ultrasonic wave, solvent, etc.

By the elastic deformation of the cylindrical fixing body 5, the hood 3 is detachably mounted to the distal end portion of the insertion section 2 of the endoscope 1. In this case, without damaging the distal end portion of the insertion section 2 of the endoscope 1 by an elastic deformation involved, the cylindrical fixing body 5 can be detachably mounted over the cap 4 so as to correspond to the distal end portion of the insertion section 2 of endoscopes of various diameters. That is, it is possible to commonly use one endoscopic hood 3 for endoscopes 1 of various diameters.

Figure 1B:
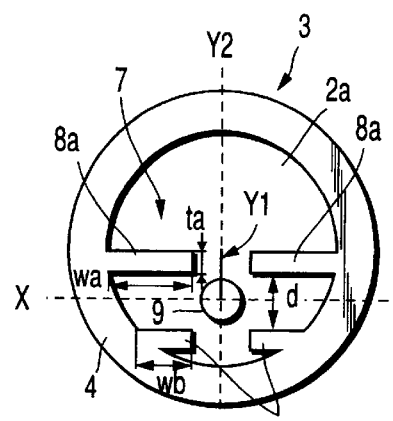
FIG. 1B is a front view showing the endoscopic hood of the first embodiment.

A rotation restricting section 7 for the treating tool 6 is provided at an inner surface of the cap 4. As shown in FIG. 1B, the rotation restricting section 7 has a pair of upper rails 8a, 8a, left and right, and a pair of lower rails 8b, 8b, left and right. The respective upper rails 8a, 8a and lower rails 8b, 8b are projected from the inner surface of the cap 4.

A channel 9 for allowing the insertion of the treating tool is provided at a distal end face 2a of the insertion section 2 of the endoscope 1. Here, the upper rails 8a, 8a and lower rails 8b, 8b are arranged each at both sides relative to a solid line Y1 passing through the axis of the insertion section 2 and the center of the channel 9 and extend in a parallel array along a dotted line x of a direction orthogonal to the solid line Y1. Therefore, the cross-sectional configuration of the cap 4 is set to such a relation that the pair of rails 8a, 8a and pair of rails 8b, 8b are arranged in a parallel array relative to the dotted line x drawn vertical to the solid line Y1 passing through the center of the channel 9 and that the distance d between the upper rail 8a and the lower rail 8b is bisected by the dotted line x.

Further, these rails 8a and 8b are set to dimensions such that, when the mucosa, etc., is to be sucked into the cap 4, the rails provide no bar to that suction. Preferably, these rails 8a and 8b are such as to have, for example, a length L of about 2 mm to 13 mm, a thickness ta of about 0.5 mm to 3 mm, the distance d between the rail 8a and the rail 8b being about 2 mm to 5 mm, a width wa of the upper rail 8a being about 1 mm to 6 mm and a width wb of the lower rail 8b being about 1 mm to 6 mm.

It is to be noted that the cap 4 and the rails 8a and 8b may be formed as separate members and be fixedly bonded together. However, it is desirable that, in view of the advantage of being lower in cost, eliminating the need to be adhesively bonded, and so on, the cap 4 and these rails 8a, 8b be formed as an integral unit with the use of the same material.

In the case where the endoscopic hood 3 is attached to the distal end portion of the insertion section 2 of the endoscope 1, it is so done in a positional relation as shown in FIG. 1B. That is, the positional relation is such that the solid line Y1 drawn in a state to pass through the center of the distal end of the insertion section 2 of the endoscope 1 and the center of the channel 9 is aligned with a dotted line Y2 drawn in a state to have the cross-sectional configuration of the cap 4 set in a mirror image (line symmetry) relation.

Figure 2A:
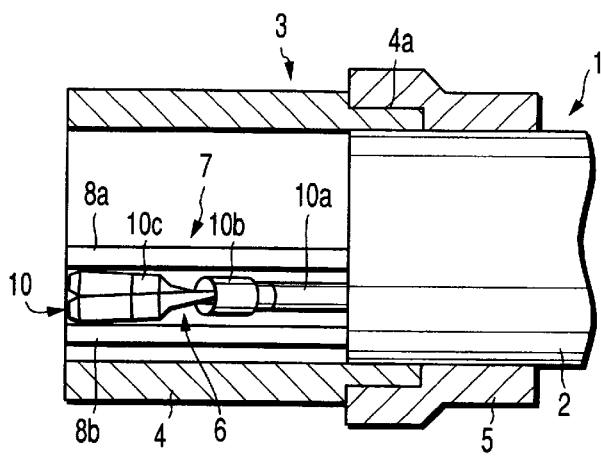
FIG. 2A is a longitudinal cross-sectional view showing a major section in a state in which a clipping device is inserted into the endoscopic hood of the first embodiment.
Figure 2B:
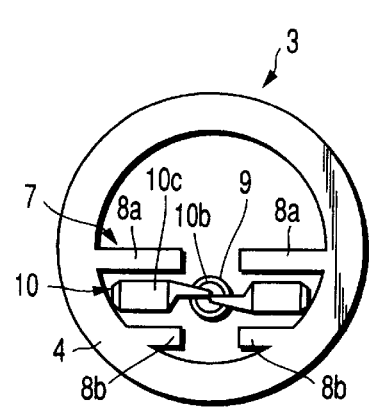
FIG. 2B is a front view of an endoscopic hood in a state in which the clipping device inserted into the endoscopic hood has its rotation restricted.

In this state, the treating tool 6 is inserted into the body of a patient via the channel 9 for allowing the insertion of the treating tool of the endoscope 1. In this case, as shown in FIGS. 2A and 2B, the treating tool 6 projected from the distal end of the insertion section 2 of the endoscope 1 is inserted in an area between the upper and lower rails 8a and 8b of the cap 4. At this time, the distal end of the treating tool 6 is abutted against the upper rail 8a or lower rail 8b of the inner surface of the cap 4 whereby the treating tool 6 is restricted from being rotated about an axial direction of the insertion section 2 of the endoscope 1.

Figure 2C:
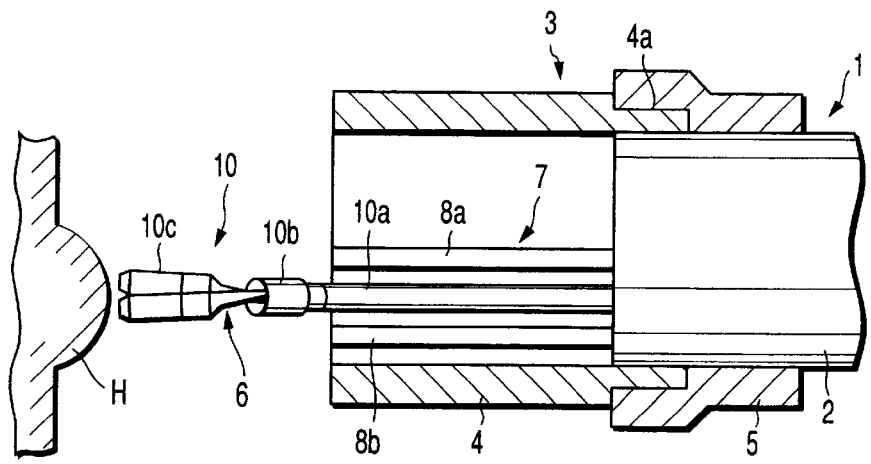
FIG. 2C is a longitudinal cross-sectional view showing a major section in a state in which the stopping of bleeding is performed with the use of the clipping device projected from the endoscopic hood of the first embodiment.

The operation of the present embodiment thus structured will be explained below. First, the hood 3 is attached to the distal end portion of the insertion section of the endoscope 1. Before the endoscope 1 is inserted into the body cavity of the patient, a corresponding treating tool 6 is so set that it is used in combination with the endoscope 1. Here, an explanation will be made about the case where a clipping device 10 as shown in FIGS. 2A to 2C is used as the treating tool 6. The clipping device 10 includes a narrow elongated flexible coil sheath 10a inserted through the channel 9 of the endoscope 1. A holding-down tube 10b is arranged at a distal end of the coil sheath 10a. Into the holding-down tube 10b a proximal end side of a clip 10c is inserted, the clip 10c having a pair of arms. The clip 10c, being drawn into the holding-down tube 10b, clips a living tissue in a body cavity of the patient.

And after the clipping device 10 has been inserted through the channel 9 of the endoscope 1, the distal end of the coil sheath 10a is projected from the distal end of the insertion section 2 of the endoscope 1. Here, the clip 10c on the distal end of the coil sheath 10a projected from the distal end of the insertion section 2 is set in a sandwiched state at an area between the upper rail 8a and the lower rail 8b of the inner surface of the cap 4 as shown in FIG. 2B. By doing so, the clip 10c of the clipping device 10 is abutted against the upper rail 8a or the lower rail 8b of the inner surface of the cap 4 to restrict the clip 10c from being rotated about the axial direction of the insertion section 2 of the endoscope 1.

After this, an operation is done for inserting the endoscope 1 into the body cavity of the patient. Then an operation, not shown, of the endoscope 1 is performed to allow the distal end's opening of the cap 4 of the hood 3 to be moved onto a region of interest where the bleeding of a living tissue H is desired to be stopped. And as shown in FIG. 2C, the clip 10c, being held in the cap 4, is projected via the distal end's opening of the cap 4 and, while being contacted with the living tissue H, abutted against the living tissue H. Or with the living tissue H drawn into the cap 4 by the suction operation of the endoscope 1, the clip 10c is abutted against the living tissue H. By operating the operation section, not shown, of the clipping device 10, the clip 10c clips the bleeding portion of the living tissue H, thus stopping the bleeding of the region of interest.

In the case where a high frequency snare 11 as shown in FIGS. 3A and 3B is used as a treating device 6, the following operation is performed. This high frequency snare 11 includes an elongated snare sheath 11a formed of a flexible tube inserted through the channel 9 of the endoscope 1, a snare wire 11b insertable back and forth in the snare sheath 11a and a loop-like section 11c on the distal end of the snare wire 11b.

Even at a time of using a high frequency snare 11, substantially the same operation as that of the clipping device 10 is performed. That is, after the hood 3 has been attached to the distal end portion of the insertion section 2 of the endoscope 1, the high frequency snare 11 is set in the endoscope 1 before inserting the endoscope 1 into the body cavity of the patient. At this time, the high frequency snare 11 is inserted through the channel 9 of the endoscope 1 and the distal end portion of the snare sheath 11a is projected from the distal end of the insertion section 2 of the endoscope 1. Here, the loop-like section 11c on the distal end of the snare sheath 11a projected from the distal end of the insertion section 2 is set in a sandwiched state at an area between the upper rail 8a and the lower rail 8b of the inner surface of the cap 4 as shown in FIG. 3B. By doing so, the loop-like section 11c of the high frequency snare 11 is abutted against the upper rail 8a or the lower rail 8b of the inner surface of the cap 4 to restrict the loop-like section 11c from being rotated about the axial direction of the insertion section 2 of the endoscope 1.

After this, an operation is performed for inserting the endoscope 1 into the body cavity of the patient. Then, the operation section, not shown, of the endoscope 1 is operated to allow the distal end's opening of the cap 4 of the hood 3 to be moved onto a to be resected region of the living tissue. And the loop-like section 11c held in the cap 4 is projected via the distal end's opening of the cap 4 and operated in such a state as to be applied to the living tissue. Or with the living tissue sucked into the cap 4 by the sucking operation of the endoscope 1 an operation is performed in a manner to apply the loop-like section 11c to the living tissue. In this state, an operation section not shown of the high frequency snare 11 is operated to allow the loop-like section 11c to be drawn back and the living tissue to be resected.

In the case where grasping forceps 12 as shown in FIGS. 4A and 4B is used as a treating tool 6, the following operation will be performed. This grasping forceps 12 includes an elongated sheath 12a inserted through the channel 9 of the endoscope 1, a pair of forceps members 12b provided to be openable and closable at the distal end of the sheath 12a, a pair of link members 12c connected to the proximal end of the forceps members 12b and an operation wire, not shown, insertable back and forth in the sheath 12a. The distal end of the operation wire is coupled to the proximal end of the link members 12c.

At a time of using the grasping forceps 12, substantially the same operation as that of the clipping device 10 is performed. That is, after the hood 3 has been attached to the distal end of the insertion section 2 of the endoscope 1, the grasping forceps 12 is set in the endoscope 12 before inserting the endoscope 1 into the body cavity of the patient. At this time, the grasping forceps 12 is inserted into the channel 9 of the endoscope 1 and the distal end of the sheath 12a is projected from the distal end of the insertion section 2 of the endoscope 1. Here, the forceps member 12b at the distal end of the sheath 12a projected from the distal end of the insertion section 2 is set in a sandwiched state between the upper rail 8a and the lower rail 8b of the inner surface of the cap 4 as shown in FIG. 4B. By doing so, the forceps member 12b of the grasping forceps 12 is abutted against the upper rail 8a or the lower rail 8b of the inner surface of the cap 4 to restrict the forceps member 12b from being rotated about the axial direction of the insertion section 2 of the endoscope 1.

After this, an operation is performed for inserting the endoscope 1 into the body cavity of the patient. Then, an operation section, not shown, of the endoscope 1 is operated to allow the distal end's opening of the cap 4 of the hood 3 to be moved onto a to be grasped region of the living tissue. In a position held into the cap 4 from the distal end's opening of the cap 4, the forceps members 12b of the grasping forceps 12 are projected to allow these members to be abutted against the living tissue or the living tissue is drawn back into the cap 4 by the sucking operation of the endoscope 1 to set these members 12b in abutting relation to the living tissue. In such a state, the operation section, not shown, of the grasping forces 12 is operated to grasp the living tissue.

The above-mentioned structure ensures the following advantage. That is, according to this embodiment, the rotation restricting section 7 is provided on the inner surface of the cap 3 attached to the forward end of the insertion section 2 of the endoscope 1. And the treating tool 6 projected from the distal end of the insertion section 2 of the endoscope 1 is set in abutting engagement with the upper and lower rails 8a and 8b of the rotation restricting section 7. This restricts the treating tool 6 from being rotated about the axial direction of the insertion section 2 of the endoscope 1. For this reason, with the use of the hood 3 at the distal end of the insertion section 2 of the endoscope 1, the rotation of the distal end of the treating tool 6 is initially restricted and it is possible to orient the treating tool 6 toward a desired direction. This offers an advantage of performing an accurate treatment quickly.

Although, in the above-mentioned embodiment, the clipping device 10, high frequency snare 11, grasping forceps 12, etc., are explained as being used as the treating tool 6, the present embodiment may be so structured as to fix the rotation of biopsy forceps for living tissue collection as in the case of the grasping forceps 12.

Although, in the endoscopic hood 3 according to the present embodiment, two pairs of rails (upper rails 8a and lower rails 8b) are provided on the inner surface of the cap 4, these may be replaced by a first variant of an endoscopic hood 3 as shown in FIGS. 5A and 5B. In the variant of the first embodiment, only one pair of lower rails 8b, right and left, are provided on the inner surface of a cap 4 and, similarly, these lower rails 8b restrict the rotation of the distal end of the treating tool 6. Here, the cross-sectional configuration of the cap 4 is so set as to define a distance of d/2 between a dotted line x drawn from the center of a channel 9 and the lower rails 8b as shown in FIG. 5B.

In the hood 3 according to this variant, the number of rails projected on the inner surface of the cap 4 can be reduced in comparison with that of the first embodiment and it is possible to suck more mucosa into the cap 4.

As shown in a second variant of FIGS. 6A and 6B, only a pair of upper rails 8a, right and left, may be provided on the inner surface of a cap 4. In this case, the rotation of the distal end of the treating tool 6 can be restricted by these upper rails 8a.

Figure 7A:
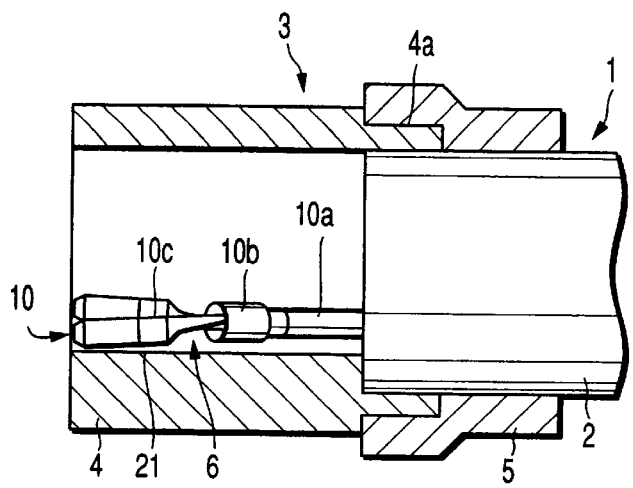
FIG. 7A is a longitudinal cross-sectional view showing a major section in a state in which a clipping device is inserted into an endoscopic hood according to a second embodiment of the present invention.
Figure 7B:
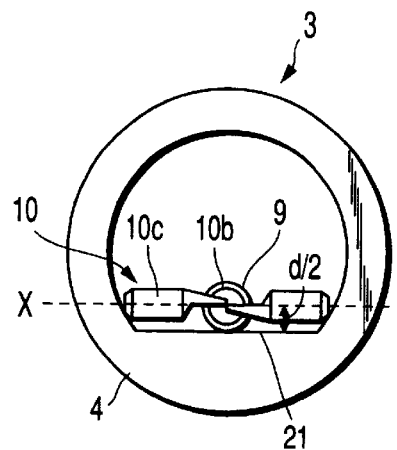
FIG. 7B is a front view of the endoscopic hood in a state in which the clipping device inserted into the endoscopic hood of the second embodiment has its rotation restricted.

FIGS. 7A and 7B show a second embodiment of the present invention. In the second embodiment of the present invention, the endoscopic hood 3 according to the first embodiment (see FIGS. 1A through 4B) is so varied as to provide a cap 4 of a different structure as will be set out below.

That is, the cap 4 of an endoscopic hood according to the second embodiment has its inner wall surface portion raised toward a center direction to provide a planar section 21. When the hood 3 is attached to the distal end of the insertion section 2 of the endoscope 1, the planar section 21 is situated in a horizontal position corresponding to a lower portion of a channel 9 of the endoscope 1 as shown in FIG. 7B. It is to be noted that the attaching of the hood 3 to the endoscope 1 is the same as that in the first embodiment and, here, an explanation of it will be omitted.

Now, an explanation will be made below about the operation of the present embodiment. First, the hood is attached to the distal end of the insertion section 2 of the endoscope 1. After this, a treating tool 6, such as a clipping device 10, is set for use in combination with the endoscope 1 before the insertion of the endoscope 1 into the body cavity of the patient.

After the insertion of the clipping device 10 into the channel 9 of the endoscope 1, the distal end of a coil sheath 10a is projected from the distal end of the insertion section 2 of the endoscope 1. Here, a clip 10c on the distal end of the coil sheath 10a which is projected from the distal end of the insertion section 2 is set in an abutted state along the planar section 21 of the inner surface of the cap 4 as shown in FIG. 7B. By doing so, the clip 10c of the clipping device 10 is abutted against the planar section 21 of the inner surface of the cap 4 to restrict the clip 10c from being rotated about the axial direction of the insertion section 2 of the endoscope 1. A subsequent operation is the same as that of the first embodiment and, here, an explanation of it is omitted.

In the second embodiment, the portion of the inner wall surface of the cap 4 is raised to provide the planar section 21. And by the planar section 21 the clip 10c of the clipping device 10 is restricted from being rotated about the axial direction of the insertion section 2 of the endoscope 1. By doing so, the cap 4 has a simpler inner configuration and has an advantage of being formed in a simpler way.

Figure 8A:
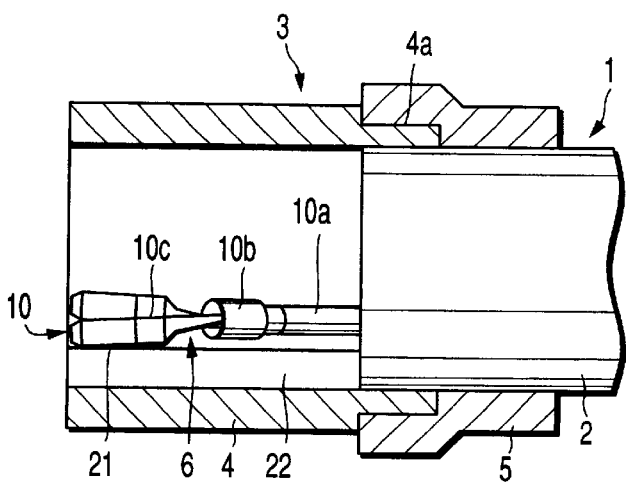
FIG. 8A is a longitudinal cross-sectional view showing a major section in a state in which a clipping device is inserted into an endoscopic hood according to a third embodiment of the present invention.
Figure 8B:
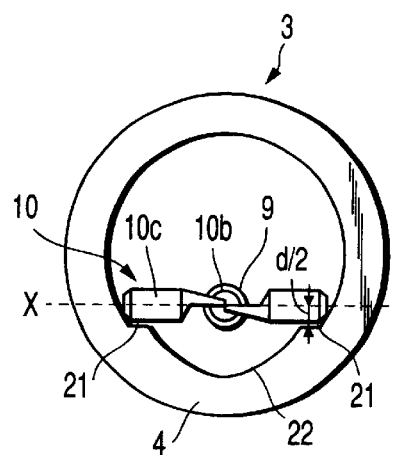
FIG. 8B is a front view of the endoscopic hood in a state in which the clipping device inserted into the endoscopic hood of the third embodiment has its rotation restricted.
Figure 8C:
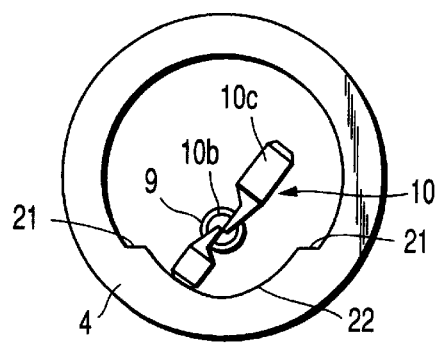
FIG. 8C is a front view of the endoscopic hood in a state in which the distal end of a treating tool in the third embodiment is rotated onto a circular arc section.

FIGS. 8A to 8C show a third embodiment of the present invention. In the third embodiment, the cap 4 of the hood 3 according to the first embodiment (see FIGS. 1A through 4B) is so varied as to provide a cap 4 of a different structure as will be set out below.

That is, according to the third embodiment, a planar section 21 similar to the planar section 21 of the second embodiment (see FIGS. 7A and 7B) is provided on the inner surface of the cap 4 and, in addition, a circular arc-like recess 22 is provided at a middle area of the planar section 21. Incidentally, attaching an endoscopic hood 3 to the endoscope 1 is the same as that in the first embodiment and, here, an explanation of it is omitted.

Now the operation of the third embodiment will be explained below. First, the hood 3 is attached to the distal end of the insertion section 2 of the endoscope 1. After this, the endoscope 1 is inserted into the body cavity of the patient. Then, with the endoscope 1 inserted into the body cavity of the patient a treating tool 6 such as a clipping device 10 is set so that it is used in combination with the endoscope 1.

This clipping device 10 is inserted via an opening on a proximal end side of the endoscope into a channel 9 provided at the endoscope 1. The clipping device 10 is set such that the distal end portion of its coil sheath 10a is projected from the distal end of the insertion section 2 of the endoscope 1. Here, a clip 10c on the distal end of the coil sheath 10a projected from the distal end of the insertion section 2 is set to a state abutted along the planar section 21 of the inner surface of the cap 4 as shown in FIG. 8B. By doing so, the clip 10c of the clipping device 10 is abutted against the planar section 21 of the inner surface of the cap 4 to restrict the clip 10c from being rotated about an axial direction of the insertion section 2 of the endoscope 1.

Now, it is assumed that, when the distal end of the coil sheath 10a is projected from the distal end of the insertion section 2 of the endoscope 1, the clip 10c enters into the circular arc-like recess 22 of the inner surface of the cap 4 as shown in FIG. 8C. In this case, the clip 10c is rotated about the axial direction within the cap 4 and, by doing so, the clip 10c of the clipping device 10 is abutted against the planar surface 21 of the inner surface of the cap 4 as shown in FIG. 8B. This prevents the clip 10c from being rotated about the axial direction of the endoscope 1.

In the operation-restricted state, the distal end of the clipping device 10 is once projected from the cap 4 and then the clip 10c is rotated about the axial direction to retract it into the cap 4. By doing so, as shown in FIG. 8C, the clip 10c of the clipping device is allowed to be readily moved into the above-mentioned recess 22.

A subsequent operation is the same as that of the above-mentioned first embodiment and an explanation of it is omitted.

As set out above, the point of time at which the clipping device 10 as the treating tool 6 is inserted into the channel 9 of the endoscope 1 can be set after the insertion of the endoscope 1 into the body cavity of the patient. Further, even if the clip 10c is projected from the insertion section 2 in such a state as not to be abutted against the planar section 21, it is possible to abut the clip 10c against the planar surface 21 by rotating the clip 10c within the cap 4.

Figure 9A:
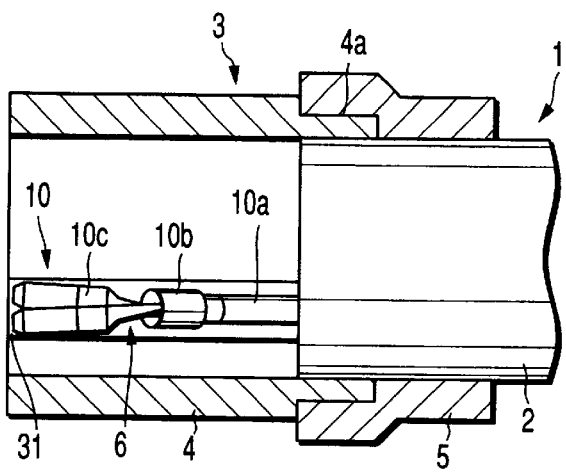
FIG. 9A is a longitudinal cross-sectional view showing a major section in a state in which a clipping device is inserted into an endoscopic hood according to a fourth embodiment of the present invention.
Figure 9B:
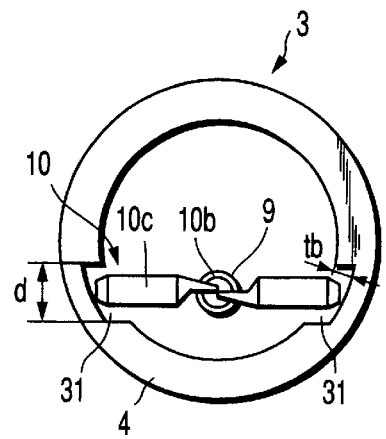
FIG. 9B is a front view showing a state in which the clipping device inserted into the endoscopic hood of the fourth embodiment has its rotation restricted.

FIGS. 9A and 9B show a fourth embodiment of the present invention. In the fourth embodiment, the hood 3 according to the first embodiment (see FIGS. 1A through 4B) is so varied as to provide a cap 4 of a different structure as will be set out below.

That is, in the fourth embodiment, a pair of recess-like engaging grooves 31, right and left, are so provided in the inner surface of the cap 4 of the first embodiment as to extend along the axial direction. The size of the respective grooves 31 is so set as to allow the treating tool 6, for example, the clip 10c of the clipping device 10, which is used in combination with the endoscope 1 to engage these grooves. Preferably, the depth tb of the engaging groove 31 is, for example, about 0.2 mm to 1 mm. Incidentally, attaching an endoscopic hood 3 to the endoscope 1 is accomplished in the same way as in the case of the first embodiment and further explanation of it is, therefore, omitted.

An explanation will be made about the operation of the resultant structure. In this embodiment, the hood 3 is attached to the distal end of the insertion section 2 of the endoscope 1. After this, the treating tool 6, for example, a clipping device 10 is so set, before inserting the endoscope 1 into the body cavity of the patient, as to be used in combination with the endoscope 1.

After the clipping device 10 is inserted through the channel 9 of the endoscope 1, the distal end of its coil sheath 10a is projected from the distal end of the insertion section 2 of the endoscope 1. A clip 10c on the distal end of the coil sheath 10a which is projected from the distal end of the insertion section 2 is so set as to be inserted in the engaging grooves 31 of the cap 4 as shown in FIG. 9B. At this time, the clip 10c of the clipping device 10 is fitted into engagement with the engaging grooves in the inner surface of the cap 4. By doing so, the clip 10c is restricted from being rotated about the axial direction of the insertion section 2 of the endoscope 1. A subsequent operation is the same as that of the first embodiment and further explanation of it is omitted.

In the above-mentioned structure, a pair of recess-like engaging grooves 31, right and left, in the inner surface of the cap 4 extend along the axial direction. For this reason, the clip 10c projected from the distal end of the insertion section 2 can be so set as to be fitted in the engaging grooves 31 of the cap 4 as shown in FIG. 9B. By doing so it is possible to restrict the clip 10c from being rotated about the axial direction of the insertion section 2 of the endoscope 1.

Further, according to this embodiment, two engaging grooves 31 are provided in the inner surface of the cap 4 and it is, therefore, possible to secure more capacity with which a living tissue, such as the mucosa, is sucked into the cap 4 and hence to obtain the advantage of sucking much more mucosa into the cap 4.

Figure 10A:
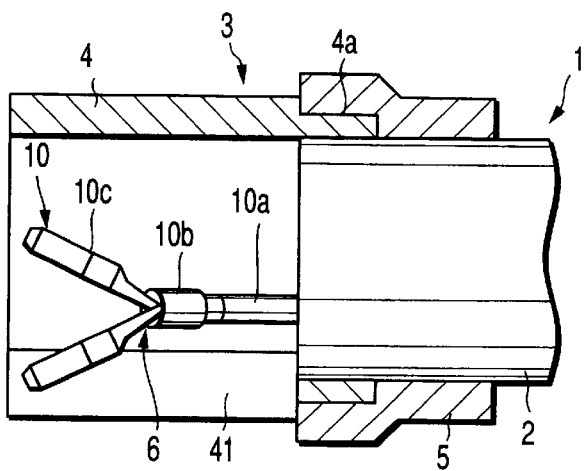
FIG. 10A is a longitudinal cross-sectional view showing a major section in a state in which a clipping device is inserted into an endoscopic hood according to a fifth embodiment of the present invention.
Figure 10B:
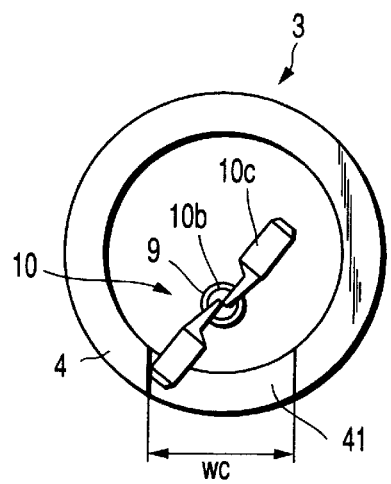
FIG. 10B is a front view showing a state in which the clipping device inserted into the endoscopic hood of the fifth embodiment is restricted from being rotated in a clockwise direction.
Figure 10C:
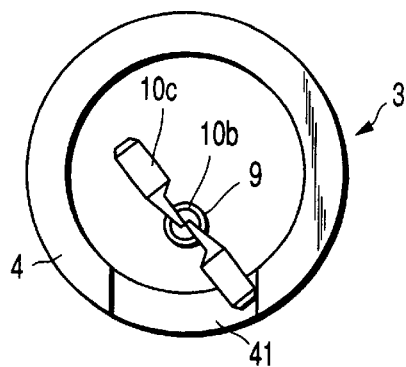
FIG. 10C is a front view showing a state in which the clipping device inserted into the endoscopic hood of the firth embodiment is restricted from being rotated in a counter-clockwise direction.

FIGS. 10A to 10C show a fifth embodiment of the present invention. In this embodiment, the endoscopic hood 3 of the first embodiment (see FIGS. 1A through 4B) is so varied as to provide a cap of different structure as will be set out below.

That is, in this embodiment, a slit 41 is formed in the inner surface of a cap 4 as a through hole extending through the inner and outer wall surface sides. In the attachment of an endoscopic hood 3 to the distal end of the insertion section 2 of the endoscope 1, the slit 41 extends along an axial direction from the distal end of the insertion section 2 of the endoscope 1 to a position of a distal end of the cap 4. As shown in FIG. 10B, the width wc of the slit 41 is, for example, about 2 mm to 12 mm and a treating tool 6, for example, a clip 10c of the clipping device 10, is used in combination with the endoscope 1 and set in an engaging relation to the slit 41. By doing so, it follows that, in a range of the width wc of the slit 41, the clip 10c is restricted from being rotated about the axial direction of the insertion section 2 of the endoscope 1. Attaching the hood 3 to the endoscope 1 is accomplished in the same way as that of the first embodiment and the further explanation of it is, therefore, omitted.

An explanation will be made about the operation of this embodiment. First, the hood 3 is attached to the distal end of the insertion section 2 of the endoscope 1. After this, a treating tool 6, for example, the clipping device 10, used in combination with the endoscope 1 is set before inserting the endoscope 1 into the body cavity of the patient 1.

After the clipping device 10 has been inserted into the channel 9 of the endoscope 1, the distal end of its coil sheath 10a is projected from the distal end of the insertion section 2 of the endoscope 1. Here, the clip 10c projected from the insertion section 2 is so set that the clip 10c is inserted into the slit 41 in the inner wall side of the cap 4 as shown in FIG. 10B. By doing so, the clip 10c engages the slit 41 in the inner wall side of the cap 4, so that, within the width wc range of the slit 41, the clip 10c is restricted from being rotated about the axial direction of the insertion section 2 of the endoscope 1.

In this state, an operation is made for inserting the insertion section 2 of the endoscope 1 into the body cavity of the patient. At this time, through the engaging of the clip 10c and slit 41, the rotation of the distal end of the clip 10c within the cap 4 can be restricted within the width wc range of the slit 41, for example, within a range of about below 900. It is to be noted that a slit may be provided in the inner wall surface of the cap 4 to allow one end of the distal end portion of the treating tool 6 to barely enter therein and the distal end of the treating tool 6 be so fixed as to allow a rotation in a given position. Further, after inserting the insertion section 2 of the endoscope 1 into the body cavity of the patient, the treating tool 6 may be inserted from a proximal end side to restrict the rotation of the distal end portion of the treating tool 6 within the hood 3.

Subsequently, the operation section, not shown, of the endoscope 1 is operated to move the distal end's opening of the cap 4 of the hood 3 to a to be clipped region of a living tissue. And the clip 10c held within the cap 4 is projected via the distal end's opening of the hood 3. By doing so, the clip 10c is so set as to be abutted against the living tissue and, in this state, the operation section of the clipping device 10 is operated to allow the living tissue to be clipped by its clip 10c.

In this embodiment, the slit 41 is formed in the inner wall surface of the cap 4 as a through hole extending through the inner and outer wall surface sides and the clip 10c on the distal end of the coil sheath 10a is set in an engaged relation to the slit 41. For this reason, within the width wc range of the slit 41, the rotation of the distal end portion of the clip 10c can be restricted to an extent of, for example, about below 900 within the cap 4. Therefore, the clip 10c is readily oriented toward a desired direction, thus offering the advantage of performing a treatment quickly.

FIGS. 11A and 11B show a sixth embodiment of the present invention. In this embodiment, the hood 3 according to the first embodiment (see FIGS. 1A through 4B) is so varied as to provide a cap 4 of a different structure as will be set out below.

That is, according to this embodiment, a pair of slits 51, right and left, is formed in the inner wall surface of the cap 4 as through holes extending through its inner and outer wall surface sides. When the hood 3 is attached to the distal end portion of the insertion section 2 of the endoscope 1, these slits 51 extend along an axial direction from the distal end of the insertion section 2 of the endoscope 1 to a position of the distal end of the cap 4. Incidentally, attaching the hood 3 to the endoscope 1 is accomplished in the same way as that of the first embodiment and, here, further explanation of it is, therefore, omitted.

An explanation will be made below about the operation of this embodiment. First, the endoscopic hood 3 is attached to the distal end portion of the insertion section 2 of the endoscope 1. After this, a treating tool, for example, a clipping device 10, is set before inserting the endoscope 1 into the body cavity of the patient so that the device is used in combination with the endoscope 1.

After inserting the clipping device 10 into the channel 9 of the endoscope 1, the distal end of a coil sheath 10a is projected via the distal end of the insertion section 2 of the endoscope 1. Here, a clip 10c on the distal end of the coil sheath 10a which is projected from the distal end of the insertion section 2 is set such that, as shown in FIG. 11B, the clip 10c is fitted in the right and left slits 51 in the inner wall surface of the cap 4. By doing so, the clip 10c of the clipping device 10 is set in an engaged relation to the slits 51 in the inner wall surface of the cap 4 to restrict the clip 10c from being rotated about the axial direction of the insertion section 2 of the endoscope 1.

In this state, an operation is made for inserting the insertion section 2 of the endoscope 1 into the body cavity of the patient. At this time, an operation section, not shown, of the endoscope 1 is operated to move the distal end's opening of the cap 4 of the endoscopic hood to a to be clipped region of the living tissue. And the clip 10c held within the cap 4 is projected via the distal end's opening of the cap 4. By doing so, the clip 10c is set in abutting contact with the living tissue and, by operating the operation section of the clipping device 10, clips the living tissue.

According to this embodiment thus structured, the pair of slits 51, right and left, are formed in the inner wall of the cap 4 as through holes extending through the inner and outer wall surface sides and the clip 10c on the distal end of the coil sheath 10a is fitted in the right and left slits 51 in the inner wall of the cap 4 to set the clip 10c in engaging contact with the slits in the inner wall of the cap 4 to restrict the clip 10c from being rotated about the axial direction of the insertion section 2 of the endoscope 1. According to this embodiment, therefore, there is no restriction against the opening width of the clip 10c within the cap 4, thus offering the advantage of clipping more living tissue.

FIGS. 12A and 12B show a seventh embodiment of the present invention. In this embodiment, the first embodiment (see FIGS. 1A through 4B) is so varied as to provide an endoscopic hood 3 having a different structure as will be set out below.

In this embodiment, the cap 4, fixing cylindrical body 5 and two pairs of rails 8a, 8b in the first embodiment are made of the same material to provide an integral unit 61. From the standpoint of a better biocompatible property and a better resistance to a chemical such as a disinfectant solution as well as a better transparent property, proper hardness, etc., the material of the integral unit 61 is made of a living tissue substance mainly consisting of a block copolymer comprising both a copolymer block mainly consisting of a vinyl aromatic compound and a block mainly consisting of a conjugate diene compound. The remaining portion of this embodiment is the same as that of the first embodiment.

Now an explanation will be made below about the operation of the present embodiment. First, an endoscopic hood 3 is attached to the distal end of the insertion section 2 of the endoscope 1. After this, a clipping device 10 as a treating tool 6 is set, before inserting the endoscope 1 into the body cavity of the patient, so that the device is used in combination with the endoscope 1. At this time, the clipping device 10 is inserted via the channel 9 of the endoscope 1 and the distal end of a coil sheath 10a is projected from the distal end of the insertion section 2 of the endoscope 1. A clip 10c on the distal end of the coil sheath 10a which is projected from the distal end of the insertion section 2 is set in a sandwiched relation between the upper rails 8a or the lower rails 8b of the inner surface of the cap 4, so that the clip 10c is restricted from being rotated about the axial direction of the insertion section 2 of the endoscope 1.

After this, an operation is performed for inserting the endoscope 1 into the body cavity of the patient. Then, an operation section, not shown, of the endoscope 1 is performed to move the distal end's opening of the cap 4 of the hood 3 to a bleeding region of a living tissue H so that the bleeding may be stopped. And the clip 10c held within the cap 4 is projected via the distal end's opening of the cap 4 and set in abutting contact with the living tissue. In this state, the operation section of the clipping device 10 is operated to clip the living tissue by means of the clip 10c.

The structure thus formed has an advantage as will be set out below. That is, according to the present invention, the hood 3 is formed of an integral unit 61 made up of a soft member. For this reason, such integral unit 61 is attached to the distal end of the insertion section 2 of the endoscope 1 and there is an advantage of readily inserting it into the body cavity of the patient.

What is claimed is:

1. An endoscopic hood which has a substantially cylindrical cap attached to a distal end of an insertion section of an endoscope to protect the distal end of the insertion section of the endoscope, the cap having a rotation restricting section in an inner surface which, when a treating tool is projected from a distal end of the insertion section of the endoscope, abuts against the treating tool to restrict the treating tool from being rotated about an axial direction of the insertion section of the endoscope.

2. An endoscopic hood according to claim 1, wherein the rotation restriction section comprises a projection projected toward an inner direction on the inner surface of the cap.

3. An endoscopic hood according to claim 2, wherein the projection comprises a planar surface with a portion of the inner surface of the cap extends toward a center direction.

4. An endoscopic hood according to claim 1, wherein the rotation restricting section comprises a wall groove portion provided by cutting a wall of the cap from the inner surface to an outer surface.

5. An endoscopic hood according to claim 1, wherein the cap is made of a hard material and has a cylindrical fixing body for fixing the distal end portion of the insertion section of the endoscope to an outer peripheral surface of a proximal end side of the cap.

6. A method of using an endoscopic hood fixed to an endoscope, the method comprising:
attaching a cap to a distal end portion of an insertion section of the endoscope to protect the distal end portion of the insertion section of the endoscope; and
restricting an axial rotation of a treating tool when the treating tool is projected from the distal end portion of the insertion section of the endoscope with an interference of a distal end of the treating tool with at least a portion of an inner wall surface of the cap.

7. A method for using the endoscopic hood according to claim 6, wherein, the interference is at least partially created by opening the distal end of the treating tool in mutually opposite directions to restrict the axial rotation of the treating tool.

8. An endoscopic hood for attachment to a distal end of an endoscope, the endoscopic hood comprising:
a body having an interior surface defining a first volume; and
treatment tool rotation restriction means cooperating with the first volume for restricting an axial rotation of a treatment tool at least partially disposed in the first volume.

9. The endoscopic hood of claim 8, wherein the treatment tool rotation restriction means comprises one or more abutments formed on the interior surface to define a second volume, the second volume being a portion of the first volume, the one or more abutments capturing a distal end of the treatment tool in the second volume so as to restrict the treatment tool from the axial rotation.

10. The endoscopic hood of claim 8, wherein the treatment tool rotation restriction means comprises one or more slits formed in the interior surface, the one or more slits defining a second volume for capturing a distal end of the treatment tool so as to restrict the treatment tool from the axial rotation.

11. The endoscopic hood of claim 8, wherein the treatment tool rotation restriction means comprises one or more abutments formed on the interior surface, the one or more abutments defining one or more planar sections to capture a distal end of the treatment tool so as to restrict the treatment tool from the axial rotation.

12. An endoscope comprising:
    an insertion section having a distal end for insertion into a body, the insertion section further having a treatment tool channel for insertion of a treatment tool; and
    an endoscopic hood for attachment to the distal end of the endoscope, the endoscopic hood comprising a body having an interior surface defining a first volume, the endoscopic hood further having treatment tool rotation restriction means cooperating with the first volume for restricting an axial rotation of a treatment tool at least partially disposed in the first volume.

13. The endoscope of claim 12, wherein the treatment tool rotation restriction means comprises one or more abutments formed on the interior surface to define a second volume, the second volume being a portion of the first volume and cooperating with the distal end of the treatment tool channel, the one or more abutments capturing a distal end of the treatment tool in the second volume so as to restrict the treatment tool from the axial rotation.

14. The endoscope of claim 12, wherein the treatment tool rotation restriction means comprises one or more slits formed in the interior surface, the one or more slits defining a second volume for capturing a distal end of the treatment tool so as to restrict the treatment tool from the axial rotation.

15. The endoscope of claim 12, wherein the treatment tool rotation restriction means comprises one or more abutments formed on the interior surface, the one or more abutments defining one or more planar sections to capture a distal end of the treatment tool so as to restrict the treatment tool from the axial rotation.

* * * * *